United States Patent [19]

Ough

[11] Patent Number: 5,443,058
[45] Date of Patent: * Aug. 22, 1995

[54] BLADE FOR TELESCOPIC LARYNGOSCOPE

[76] Inventor: Yon D. Ough, 2350 E. Ridge Rd., Beloit, Wis. 53511

[ * ] Notice: The portion of the term of this patent subsequent to Nov. 23, 2010 has been disclaimed.

[21] Appl. No.: 186,445

[22] Filed: Jan. 24, 1994

Related U.S. Application Data

[63] Continuation-in-part of Ser. No. 156,003, Nov. 22, 1993, which is a continuation-in-part of Ser. No. 564,375, Aug. 8, 1990, Pat. No. 5,263,472, which is a continuation-in-part of Ser. No. 357,976, May 26, 1989, abandoned.

[51] Int. Cl.⁶ ............................................. A61B 1/26
[52] U.S. Cl. .................................. 600/188; 600/190; 600/245
[58] Field of Search .................. 128/6, 10, 11, 16, 19, 128/23, 200, 26

[56] References Cited

U.S. PATENT DOCUMENTS

| | | | |
|---|---|---|---|
| 4,905,669 | 3/1990 | Ballard et al. | 128/11 |
| 4,947,829 | 8/1990 | Ballard | 128/11 |
| 5,261,392 | 11/1993 | Wu | 128/11 |
| 5,263,472 | 11/1993 | Ough | 128/11 |

*Primary Examiner*—Mark S. Graham

[57] ABSTRACT

An improvement for laryngoscope blades is disclosed, for expanding the field of view beyond that directly visible to a person performing intubation. A small endoscope is provided, slidably attached to the blade, and includes an eyepiece near the laryngoscope handle and a front lens near the blade tip. The endoscope is adapted to expose for remote viewing through the eyepiece an additional field of view generally above and beyond the blade tip. The endoscope is slidably attached to the blade so that the endoscope can be advanced and retracted when and as required to assist intubation. The blade includes an upper protrusion extending outwardly from the blade spoon, and a ridge depending downwardly from the protrusion for shielding the front lens of the endoscope from tissue surrounding the lens.

8 Claims, 6 Drawing Sheets

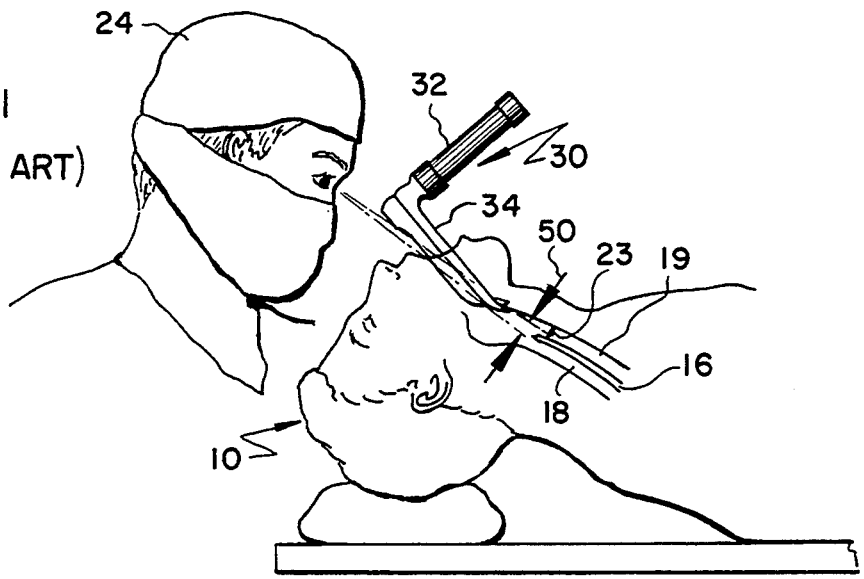
FIG. 1 (PRIOR ART)
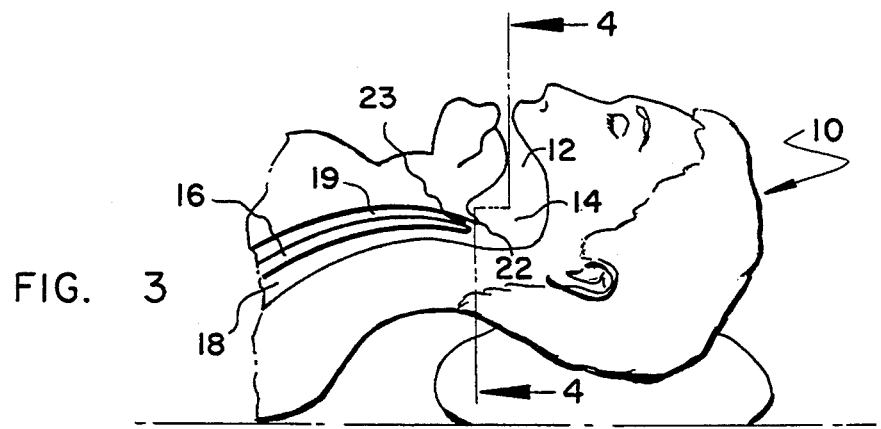
FIG. 2 (PRIOR ART)
FIG. 3

FIG. 4
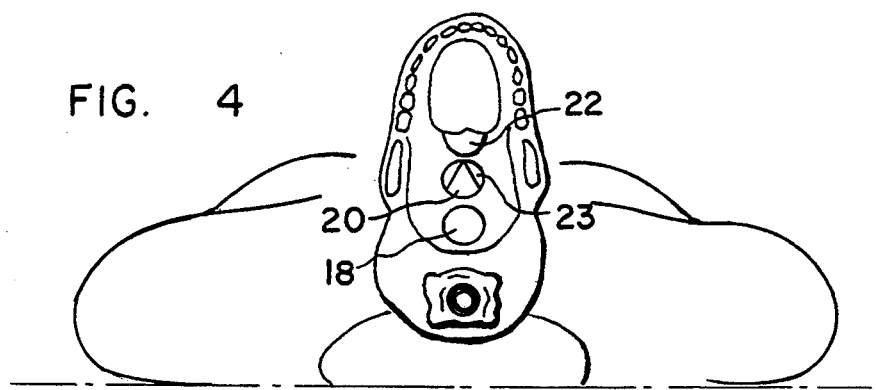
FIG. 5
(PRIOR ART)
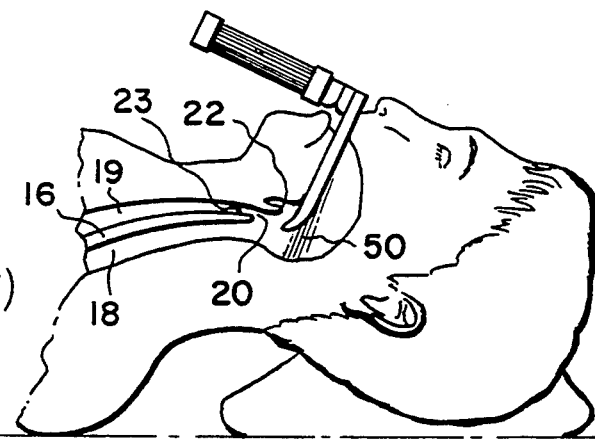
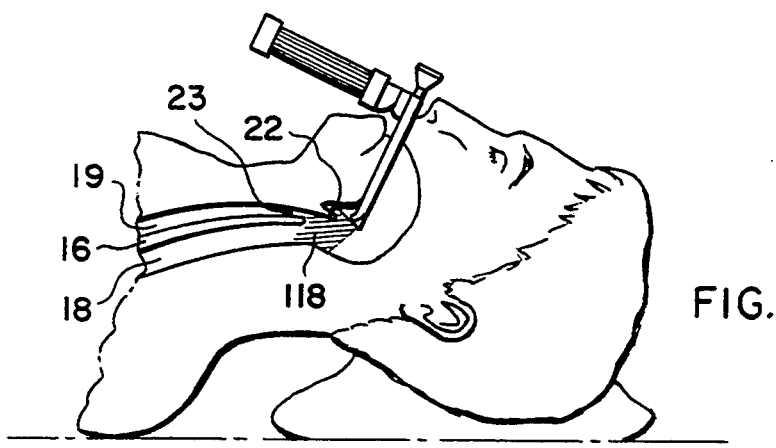
FIG. 6

BLADE FOR TELESCOPIC LARYNGOSCOPE

RELATION TO OTHER APPLICATIONS

This application is a continuation-in-part of co-pending U.S. patent application Ser. No. 08/156,003 filed Nov. 22, 1993 for a "Telescopic Laryngoscope Blade", which is a continuation-in-part of U.S. patent application Ser. No. 07/564,375 filed Aug. 8, 1990, for an "Improved Laryngoscope Blade", now U.S. Pat. No. 5,263,472, which is a continuation-in-part of U.S. patent application Ser. No. 07/357,976 filed May 26, 1989, for a "Laryngoscope Blade" now abandoned.

BACKGROUND OF THE INVENTION i. Technical Field

This invention pertains generally to the field of medical instruments, and more particularly to an improved laryngoscope blade for aiding a medical practitioner performing endotracheal intubation, particularly during difficult intubations.

ii. Technical Background

During patient medical care, often it is necessary to insert an endotracheal tube for respiratory support of a patient in distress. For example, a patient under general anesthesia is unable to maintain unassisted respiration, and an endotracheal tube connected to a respirator will be inserted in the patient's trachea to perform respiratory support. Endotracheal intubation also is performed frequently on critically ill patients who are unable to breathe effectively on their own, and on patients who are unable to protect their airway from vomitus from the stomach.

Endotracheal intubation procedures, which may be orotracheal wherein the endotracheal tube is inserted through the mouth of the patient, or nasotracheal wherein the endotracheal tube is inserted through the nose of the patient, are a routine part of the daily practice of an anesthesiologist. For other health care professionals, such as paramedics and other physicians, the procedure is less routine and performed less often. For all who perform the procedure, even under ideal conditions, intubation can be highly stressful. When intubation is performed to support a non-breathing patient, brain damage or death resulting from inadequate supply of oxygen can occur within four minutes. Clearly, intubation must be completed rapidly.

During endotracheal intubation, the glottic opening, which is defined by the glottis or vocal cords and surrounding structures, must be identified, so that the tube is correctly inserted through the glottic opening and into the trachea. Positive identification of the glottic opening minimizes the possibility of esophageal intubation and the potential of hypoxic brain damage.

A laryngoscope is the instrument used to assist intubation, and typically includes a handle and detachable blade disposed at near right angle. Numerous different types of blades are available, including straight and curved types. Most practitioners tend to favor one or the other of the common blades, and will use it in the vast majority of procedures. The blade is inserted into the mouth of the patient, holding the mouth in a fully open position and the tongue against the floor of the mouth. The epiglottis frequently is elevated, either through direct contact by the laryngoscope blade or indirectly by raising hypopharyngeal tissues. Under normal circumstances, this will expose the epiglottis and glottic opening to allow direct observation by the practitioner who sights along the laryngoscope blade. A light on the blade illuminates the visual field.

For perhaps one intubation of every one-hundred, anatomical variance in the patient causes difficulties. In some patients, the glottis is located anteriorly, placing the glottic opening out of the normal field of view. In other patients, such as those having small mouths or mandibular joint dysfunctions, the mouth can not be opened sufficiently for the desired positioning of the laryngoscope blade, and the field of view presented will be limited to the regions of the oropharynx. Occasionally, these conditions are anticipated, and adequate precautions can be taken. Often, however, the condition is not recognized until the intubation procedure has been started. In a patient having elective surgery, such a condition can pose a life-threatening situation for an otherwise healthy patient.

Drastic steps may become necessary to complete the intubation procedure before brain damage or death results from oxygen deprivation. Forcing the laryngoscope blade deeper into the hypopharynx may result in excessive pressure being applied against the teeth of the patient, causing the teeth to crack or break. After beginning the procedure with standard instruments, it may become necessary to use specialized instruments to complete the procedure. Preparing and switching instruments wastes much of the limited time available for intubation, and results in even the most experienced practitioner being forced to use instruments with which he is less experienced. Further, some such specialized instruments, such as flexible fiber-optic devices, can not be used on infants because of size.

Intubation under abnormal conditions becomes highly stressful for everyone involved, including the most experienced practitioners, which may further reduce efficiency and performance.

In my aforementioned U.S. Pat. No. 5,263,472, I disclosed an improved laryngoscope blade having a telescope affixed to the blade. The telescope includes an eyepiece near the laryngoscope handle, a barrel extending along the blade and a front lens near the distal end of the blade. This improved blade has been found to be of great assistance in the vast majority of difficult intubations. However, in some of the most difficult intubations, even the improved blade of my previous invention has not adequately revealed the glottic opening. On curved blades, the fixed telescope is widely spaced from the upwardly curved tip of the blade, and may make the overall end structure of the blade too large for proper insertion. The front lens, fixed in position can be fouled by tissue or secretions. The fixed telescope on each blade makes the blades expensive.

In my aforementioned co-pending U.S. patent application Ser. No. 08/156,003, I disclosed a telescopic laryngoscope blade in which the endoscope is adjustable in position relative to the blade, and can be moved forward and reward relative to the blade tip. While my telescopic blade works well for optimally positioning the endoscope for viewing the glottic opening, under some conditions, especially when the endoscope is extended relatively far forward, tissue and secretions can foul the objective lens, hampering viewing.

SUMMARY OF THE INVENTION

It is therefore one of the primary objects of the present invention to provide a laryngoscope which expands the visual field for one performing intubation beyond that field presented for direct, unassisted observation through the mouth of the patient, and which can be used as a standard instrument during normal, day to day procedures.

Yet another object of the present invention is to provide a visual field expanding laryngoscope blade that is suitable for use on infants, children and adults, which provides a panoramic view of the hypopharynx even when the patient's mouth is opened only minimally and which reduces the risk of dental injury to the patient and the risk of trauma resulting from repeated, unsuccessful attempts to complete intubation.

A further object of the present invention is to provide a laryngoscope blade that exposes, for indirect observation, regions above and beyond the blade tip, which can be adjusted in position when required to reveal the glottic opening, which simplifies abnormal intubation procedures for both well-experienced and lesser-experienced practitioners, and which simplifies intubation kits by minimizing the need for specialized equipment.

Yet a further object of the present invention is to provide a laryngoscope blade having an adjustable mechanism for indirect viewing of regions of the hypopharynx, which mechanism is easily and conveniently used even in the most difficult cases, and which minimizes fouling of the objective lens by tissue or secretions.

These and other objects are achieved in the present invention by providing on the blade an endoscope that is adjustable in position relative to the blade. The endoscope includes an eyepiece in the general region of the connection between the laryngoscope handle and the laryngoscope blade, a barrel extending along the blade, and a front or objective lens near the distal end of the blade. Suitable optical properties are provided in the endoscope so that the visual field presented through the endoscope is generally above and in front of the endoscope. The endoscope is attached to the blade by a sleeve or one or more collars that are affixed to the blade. The endoscope can be moved forward and rearward in the sleeve as necessary. One or more lights can be provided to illuminate the telescopic visual field as well as the standard visual field. The blade is shaped to protect the objective lens, shielding the lens from tissues and secretions in both the retracted and advanced positions.

The blade can be used for standard, routine intubation procedures, and allows direct observation through the mouth similar to a standard blade of the same general type. If it becomes apparent that direct observation is inadequate for completing intubation, one performing the procedure, without changing instruments, can look through the endoscope at a region not observable through direct observation. Sliding the endoscope in the sleeve or collars allows the practitioner to precisely position the endoscope to reveal the glottic opening. Rotating the laryngoscope or the endoscope can provide a panoramic view of the hypopharynx, allowing further visual examination of the region.

Additional objects and advantages of the present invention will be apparent from the detailed description and the accompanying drawings.

BRIEF DESCRIPTION OF THE DRAWINGS

FIG. 1 is a perspective view of a patient in position for routine intubation, showing some internal anatomical structures, a laryngoscope according to the prior art positioned for intubation and a person viewing along the laryngoscope blade into the patient's mouth.

FIG. 2 is a perspective view of a straight laryngoscope blade of the prior art.

FIG. 3 is a perspective view of a patient on which certain anatomical features are identified.

FIG. 4 is a cross-sectional view of the patient shown in FIG. 3, taken along line 4—4 of FIG. 3.

FIG. 5 is a view similar to FIG. 1, but showing the field of view in a patient having a glottis of pronounced anterior location.

FIG. 6 is a view of the patient shown in FIG. 5, but indicating the additional field of view presented through use of the present invention.

DETAILED DESCRIPTION OF THE PREFERRED EMBODIMENT

Figure 7:
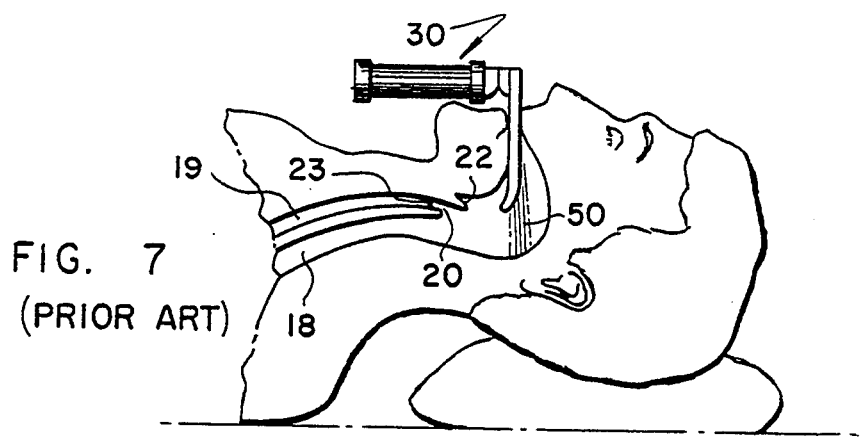
FIG. 7 is a view again similar to that of FIG. 1, but showing the field of view presented in a patient whose mouth can not be opened wide.

Referring now more specifically to the drawings, and to FIG. 3 in particular, a patient 10 is shown, having been placed in the sniffing position in preparation for intubation. The oropharynx region of the patient is generally indicated by the numeral 12, and the hypopharynx by the numeral 14. During intubation, a tube is inserted through the nose of the patient (nasotracheal intubation) or through the mouth of the patient (orotracheal intubation) and into the trachea 16 leading to the lungs. The tube is then connected to equipment for providing respiratory support.

It is essential during intubation that the endotracheal tube not be inserted in the esophagus 18 which leads to the stomach, in the mistaken belief that the trachea has been located. The opening from the hypopharynx 14 to the larynx 19 is the glottic opening, identified in FIG. 4 by the numeral 20. To distinguish the glottic opening from the esophagus below it, the practitioner performing intubation looks for and identifies the epiglottis 22, a small flexible body in front and above the glottis 23. Identification of the epiglottis clearly indicates the location of the glottic opening. Failure to locate and identify the glottis makes intubation a random, risky procedure.

The practitioner 24 performing intubation is positioned at the head of the patient and uses a laryngoscope 30 to aid observation of the anatomical structures and identification of the glottic opening. The laryngoscope includes a handle 32 and a blade 34. The blade 34 includes a first or connecting end 36 having a fixture 38 for mating attachment with a complementary fixture 39 of the handle 32. Such attachments are common and well known in the art, and will not be described in further detail herein. The blade 34 further includes a second, distal end or tip 40 that is passed through the patient's mouth and at an angle into the hypopharynx during the intubation procedure.

In FIG. 2 as an enlarged view, and in other Figures illustrating the prior art, a standard, straight blade is shown, substantially illustrative of the blade embodiment commonly referred to as a Miller blade. Other common, straight blade types are known as Wisconsin, Oxiport-Miller, Schapira, Snow, Phillips, Whitehead, Eversole, Flagg, Guedel and Bennett blades. All include a substantially straight body member 42. The illustrated Miller blade has a generally flat flange portion 44 and a semi-cylindrical body portion 46 converging and terminating at the distal end 40. Others of the straight blades have varying shapes and contours, although extending generally in a straight orientation.

Figure 13:
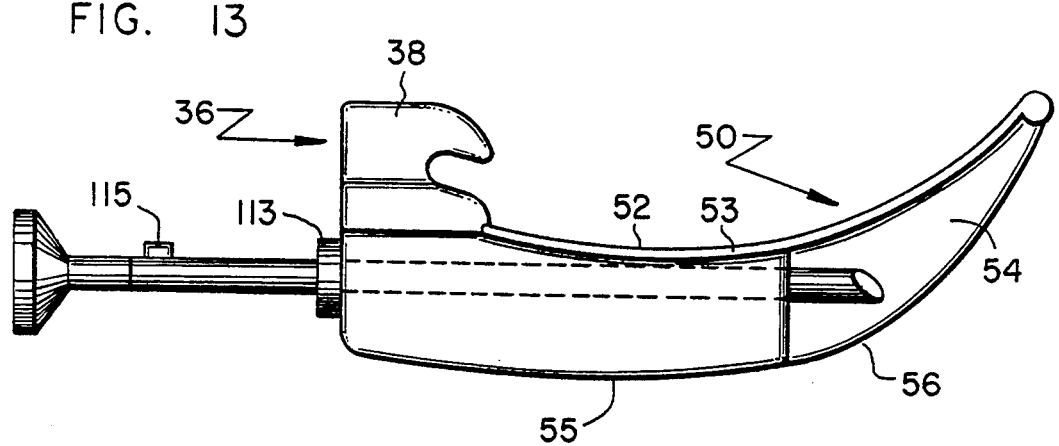
FIG. 13 is a side elevational view of a curved laryngoscope blade embodying the present invention, showing the endoscope in its retracted position.
Figure 14:
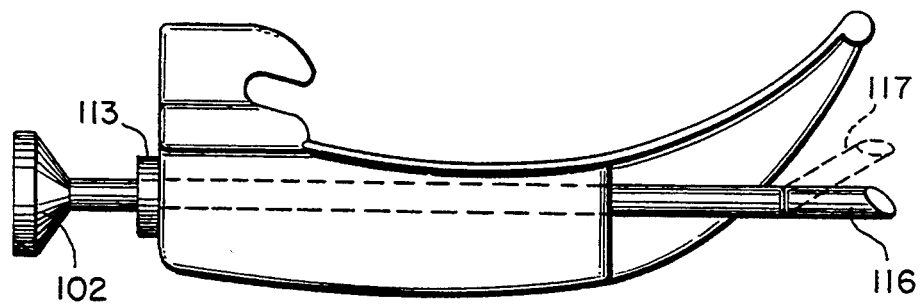
FIG. 14 is a side elevational view of the curved blade shown in FIG. 13, but with the endoscope in extended position.
Figure 15:
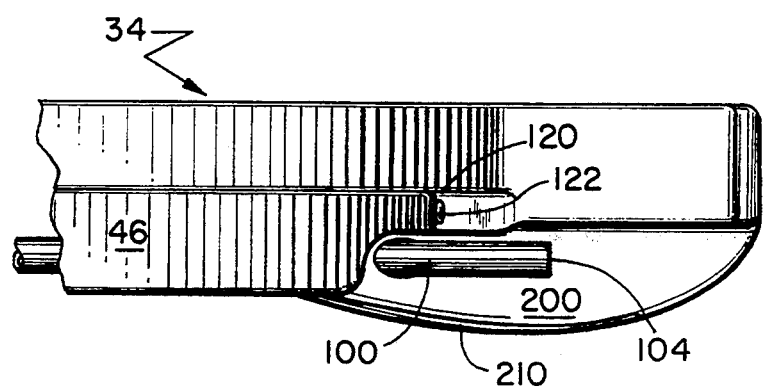
FIG. 15 is a fragmentary bottom plan view of a curved blade embodying the improved blade design of the present invention.
Figure 16:
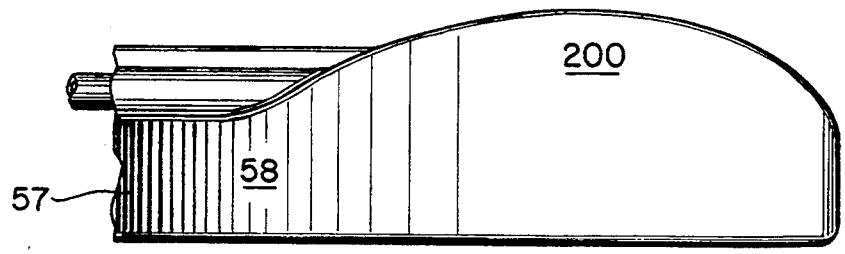
FIG. 16 is a fragmentary top plan view of the blade shown in FIG. 15.

The straight blade embodiments may be contrasted with curved blade embodiments that have a pronounced arc. The present invention is particularly advantageous when used for curved blades for which many other adaptations have not been successful. Common curved blades are known as Macintosh and Siker blades. Curved blades are shown in FIGS. 13, 14 and 15, modified according to the present invention. Curved blades include a similar connecting end 36 and fixture 38 for mating attachment to a fixture 39 of the handle 32. An arced body portion 50 of the blade includes a top surface 52 of a curved, generally horizontally disposed body portion 53, with a generally vertically disposed body portion 54 disposed along one edge thereof. The vertical body portion 54 may have a wider section 55 near the connecting end 36 and a narrower section 56 near the distal end 40. Similarly, the horizontally disposed body portion 53 may be wider in a section 57 near the connecting end than in a section 58 near the distal end.

All of the blades, both straight and curved, are available in different sizes for children and adults. The choice of blade styles, including the choice between curved and straight, is normally one of personal preference. The present invention can be adapted for use on various size blades.

During normal intubation, the distal end 40 of the blade, whether curved or straight, is used directly or indirectly to elevate the epiglottis 22, revealing the glottic opening 20. Straight blades, which are longer, can be inserted to contact and directly elevate the epiglottis. Curved blades, which normally are shorter, when inserted reach short of the epiglottis. The curved blades lift the tongue and hypopharyngeal tissues, thereby indirectly elevating the epiglottis. Such normal intubation is illustrated in FIG. 1, with the general view available to the practitioner 24 by sighting through the semi-cylindrical body portion 46 along the straight blade 34 being illustrated by field of view 50.

Referring now to FIGS. 9 through 15, the present invention can be seen, and includes a fiber optic endoscope 100 connected to the blade 34. The endoscope includes an eyepiece 102 disposed near the first or connecting end 36 of the blade and a front or objective lens 104 disposed at the distal end 40 of the blade. A barrel 106, preferably having optical fibers therein, extends between the eyepiece and the front lens. The precise location of the endoscope may vary depending on the design of the blade in which it is incorporated. Normally, the endoscope is disposed slightly left of the mid-line of the blade.

While a fiber optic endoscope is preferred, a conventional telescope can also be used as the endoscope. The endoscope may or may not provide magnification. In adults it may be adequate to provide remote, indirect viewing as will be described subsequently, without significant magnification. In children and for some specific procedures, magnification may assist the practitioner in performing intubation and in examining the hypopharynx.

The objective lens 104 is disposed and optically adapted to expose to the practitioner viewing through the endoscope a region generally above and beyond the distal end of the blade. Such small endoscopes are known for use in other medical procedures such as cystoscopy, bronchoscopy, sinusendoscopy and laproscopy. and are available with various angles of observation, including ones having center lines of the telescopic field of view 118 being, for example, twelve degrees, thirty degrees, seventy degrees and ninety degrees from a line directly in front of the endoscope axis. It is believed that an endoscope having at least about a thirty degree angle will be sufficient for the present invention, and a so-called seventy degree endoscope also may be used. However, other angles of sight in the endoscope also can be used advantageously.

The endoscope is slidably attached to the blade by a retention device 113 such as a sleeve, grommet, ring, collar or housing that is affixed to the blade near the connecting end 36 and through which the endoscope can be slid. A grommet, collar or ring of rubber, plastic or other such elastic material works particularly well in allowing the endoscope to be slidably adjusted forward and back while securing the endoscope in place once positioned. The elastic material, if properly fitted around the endoscope, resists accidental and unintended movement of the endoscope. In one embodiment, a retention device comprising a tube affixed to the blade, with a tightly fitting elastic nipple at one end has worked effectively in holding the endoscope in position, while allowing easy adjustment.

The endoscope can be withdrawn completely from the retention device for cleaning, repairing or replacing. When preparing the laryngoscope for the intubation procedure, the blade is attached to the handle, and the endoscope is inserted in the retention device, with the end of the endoscope being kept well rearward from the blade distal end unless needed. In this fully retracted position the objective lens of the endoscope is protected from fouling by secretions.

In the retracted position, the objective lens can be held well rearward of the blade tip so as not to interfere with routine intubation. When required to expose a field of view not available through direct observation, the endoscope can be advanced forward by pushing on the end near the eyepiece, to slide a portion of the barrel through the retention device 113.

To ensure proper orientation of the endoscope, so that the angular front lens is directed in the proper way, the endoscope barrel and the retention device can be shaped to allow the endoscope to be inserted in only one way. Alternatively, other guide means, such as groove and groove followers can be used.

To prevent the endoscope from being advanced too far inadvertently, a stop 115 is provided on the endoscope barrel. The stop 115 may be in the from of a collar, knob or other protrusion of diameter or extension greater than the barrel of the endoscope to abut against the retention device 113 and prevent continued advancement of the endoscope. The retention device 115 is located on the endoscope barrel to allow the endoscope to be advanced such that the objective lens is at the end of the blade or only minimally there beyond.

To even further minimize the danger of inadvertent injury to oral tissues by poking from the endoscope, at least a portion 116 of the endoscope at the objective lens end is made of pliable, soft material to yield to pressure exerted thereon if oral tissues are encountered during advancement of the endoscope. Fiber optic endoscopes having such physical properties are known in the medical field, and will not be described in greater detail herein.

For the most difficult situations, a further advantageous feature of the present invention, found in fiber optic endoscopes for other procedures, includes the ability, through activation by rotation of an activating arm not shown, to curve the objective lens end of the endoscope. This feature is shown by dotted lines in FIG. 14, wherein the numeral 117 designates the curved position indicated by dotted lines. Curving the objective lens end of the endoscope in this manner further adjusts the field of view available through the endoscope.

The present invention includes an improved blade, wherein the shape of the blade is modified to provide protection for the objective lens of the endoscope. It has been found that the tongue or other tissues can inadvertently come in contact with the objective lens of the endoscope either while the blade is being positioned in the mouth or, more frequently, as the endoscope is being advanced and properly positioned for viewing the glottic opening. Blades of the present invention include a slight protrusion 200 along the upper surface, or spoon portion, of the blade to prevent the tongue or other tissues from sliding or wrapping around the blade and coming in contact with the endoscope objective lens. The protrusion need not be large, and will adequately protect the endoscope without interfering with placement or use of the blade. The protrusion curves outwardly from near the front edge of the blade and rearwardly therefrom in a gently curving arc.

To further protect the endoscope objective lens, a ridge 210 is provide extending along the side of the blade, generally at the outer edge of the protrusion 200. The ridge 210 extends downwardly from the protrusion and further inhibits the tongue or other tissues from wrapping around the blade and prevents tissues along the side of the blade from coming into contact with the objective lens. In this manner the objective lens is kept clean and free from secretions present on the surrounding tissues.

In conventional laryngoscope blades, lights are provided to illuminate the standard field of view 50. Commonly, batteries in the handle supply energy to illumination units disposed toward the distal end of the blade. While various methods of supplying and directing the light can be used, state of the art laryngoscopes use an optical fiber and illumination unit disposed along the blade length.

In the present invention, it is desirable to provide a second illumination unit 120 near the distal end of the blade to illuminate the telescopic field of view 118. A branch optical fiber 122 is extended to the illumination unit 120.

Advantageous use of the present invention can be seen by comparing various drawings. In FIG. 5 a patient having an anteriorly located glottis is shown. In such a situation, during attempts at intubation the standard visual field of view 50 does not include the epiglottis, glottic opening or the like. The natural tendency of one performing intubation of such a patient is to pull the end of the handle 32 toward the patient's forehead, in an attempt to expose the glottic opening. This can place excessive pressure against the teeth of the patient, even cracking or breaking them. During difficult intubations, such dental injuries are not uncommon.

In FIG. 6, the telescopic field of view 118 made available by the present invention extends above and beyond the blade distal end. This expanded field of view includes the epiglottis and glottic opening. Intubation can be completed without forcing the laryngoscope against the patient's teeth.

In FIG. 7, an even more difficult intubation is illustrated. Due to anatomical conditions, the patient's mouth can be opened only minimally. Without placing excessive pressure against the patient's teeth, the laryngoscope blade can be inserted only substantially straight, and not angled toward the epiglottis as required. The standard field of view 50 available when the laryngoscope is in this position does not expose the epiglottis and glottic opening.

Figure 8:
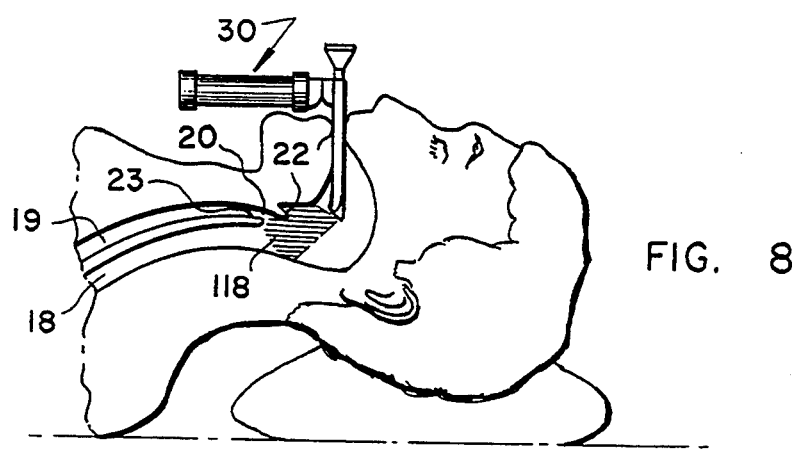
FIG. 8 is a view of the patient shown in FIG. 7, but indicating the additional field of view presented through use of the present invention.
Figure 9:
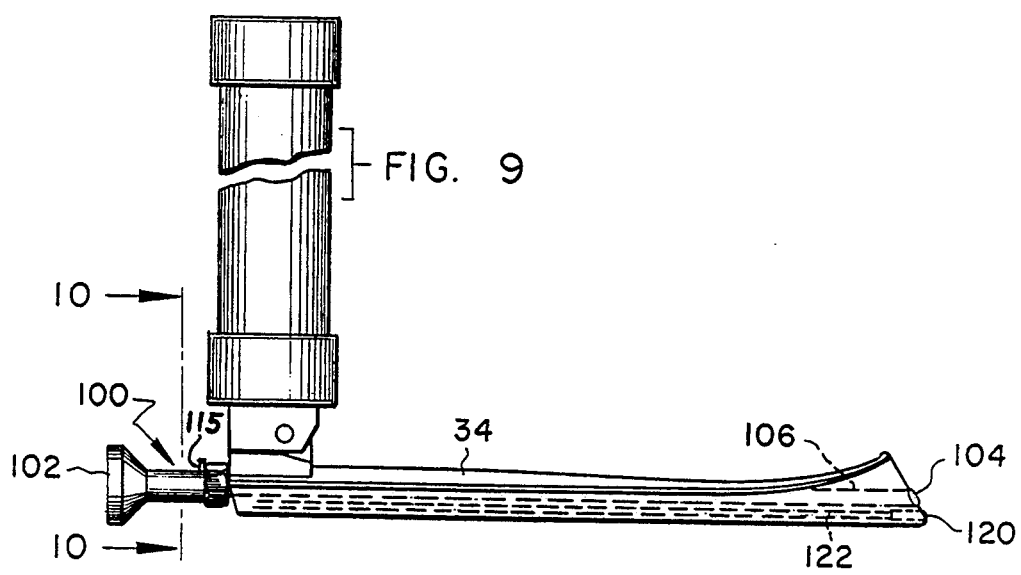
FIG. 9 is a side elevational view of a laryngoscope having a straight blade according to the present invention.
Figure 10:
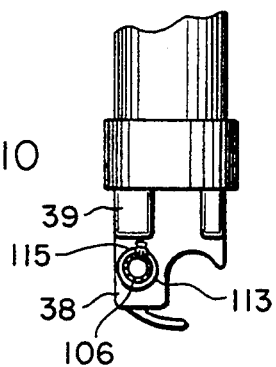
FIG. 10 is a cross-sectional view of the laryngoscope shown in FIG. 9, taken along line 10—10 of FIG. 9.
Figure 11:
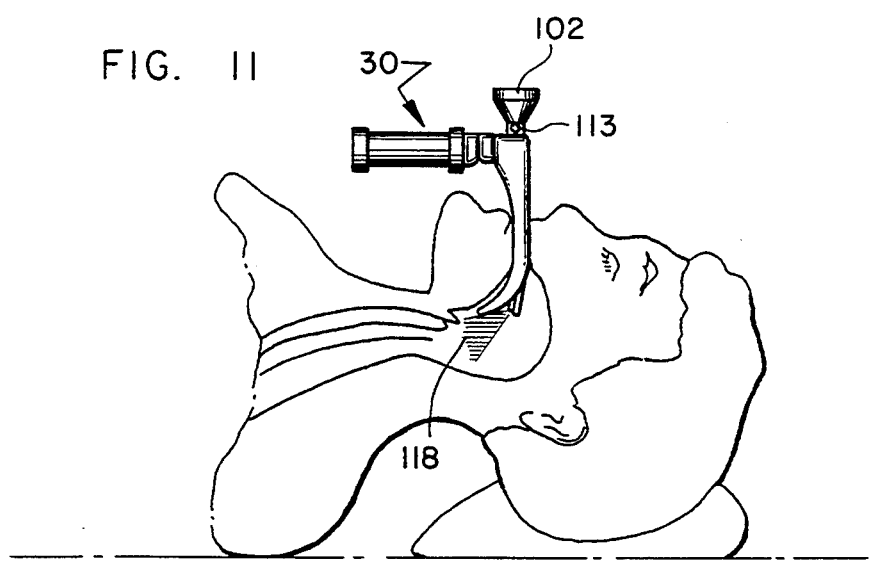
FIG. 11 is a view similar to that of FIGS. 1 and 7, but showing the field of presented through use of the present invention on a curved blade.
Figure 12:
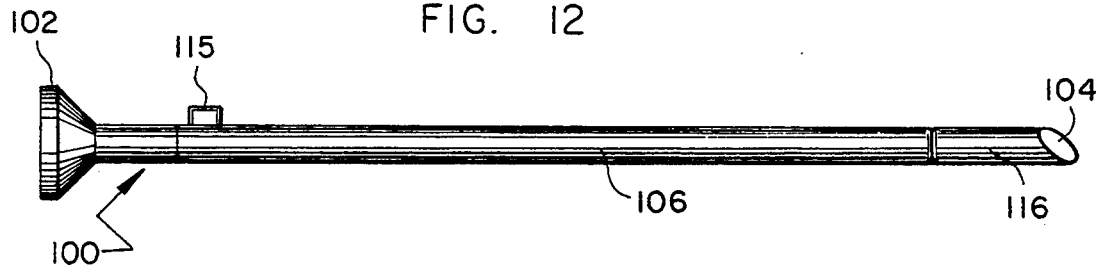
FIG. 12 is an enlarged view of an endoscope used in the present invention.

Even under the extreme conditions illustrated in FIG. 7, the endoscope assisted blade clearly exposed the epiglottis and glottic opening. The field of view 118 is again directed toward the glottic opening as shown in FIG. 8. The illumination unit 120 near the distal end of the blade provides light for completing the intubation procedure.

In the use and operation of a laryngoscope blade embodying the present invention, medical practitioners who perform intubation can use the modified blade of their choice, with endoscope in place, for all intubation procedures, even when the expanded field of view presented by the endoscope is not necessary. The endoscope will be retained in a retracted or withdrawn position, with the objective lens thereof rearward from the distal end of the blade.

If difficulties are encountered in locating and identifying the glottic opening through direct, unassisted observation, the practitioner can immediately adjust to direct the examination through the endoscope eyepiece, thereby availing himself or herself of the expanded field of view through the endoscope. Switching from the unassisted view available by direct observation through the mouth, to the expanded telescopic view can be done quickly, without the need to change instruments or even remove the laryngoscope from the patient's mouth. The endoscope can be advanced forward from its retracted position, sliding the endoscope barrel in the retention device 113. The endoscope can be advanced while the practitioner observes through it, without danger of inadvertently advancing it too far and injuring oral tissues. As the endoscope is advanced, with the practitioner looking through it, anatomical landmarks can be observed, making identification of the glottic opening quick and easy. The flexible endoscope tip reduces the potential for injury to tissue encountered, and the stop 115 prevents over advancement of the endoscope. Thus, the practitioner can position the endoscope in the most advantageous position quickly, while observing the field of view presented. This eliminates waste of time in positioning the endoscope and maximizes the time available for completing difficult intubation.

The present invention reduces the risk of trauma through its ready availability and its simplicity of use. Some practitioners may choose to use the telescopic view during normal intubation. The constant availability of the endoscope allows the practitioner to periodically use the endoscope even when not required, thereby maintaining a high level of skill in its use. Further, advantages of the endoscope will be used more readily as a result of its availability, thereby reducing trauma resulting when the practitioner's view is obstructed and undue pressure is exerted against teeth or repeated unsuccessful attempts are made at completing intubation, injuring oral tissues.

The endoscope can be used on various types and sizes of blades. When the endoscope is retracted, the blade is no different in size than a standard blade of the same type, and initial placement of the blade is the same as for a standard blade. By minimizing the need for special, infrequently used instruments, intubation kits are simplified. No unusual techniques or skills are required to use the invention except for familiarity in manipulating and inserting the endotracheal tube in coordination with an indirectly viewed field. Thus, in difficult intubation, the present invention is easier to use than other specialized instruments previously available, particularly for those who perform intubations infrequently.

Slight tilting and rotation of the laryngoscope and rotation of the endoscope enable the practitioner to examine the hypopharynx closely and may assist in other procedures.

The modified shape of the blade of the present invention, including the protrusion 200 and the ridge 210 protect the objective lens of the endoscope from becoming smeared with fluids on the surrounding tissues by holding the tissue away from the lens during use of the laryngoscope.

While several embodiments of a telescopic laryngoscope blade have been shown and described herein, it should be understood that various changes may be made without departing from the scope of the present invention.

I claim:

1. A telescopic laryngoscope blade comprising:

a body shaped for insertion through a patient's mouth to depress the patient's tongue during endotracheal intubation;

said body having a connecting end adapted for connecting said blade to a laryngoscope handle, and a distal end extending into the hypopharynx of the patient being intubated, said body being shaped to elevate the epiglottis and to expose the glottic opening of the patient for direct visual observation alongside the blade during routine normal intubation;

an endoscope disposed along said body;

said endoscope including an eyepiece at one end of an endoscope barrel, and a front lens at an end of said barrel opposite said eyepiece and near said distal end of said blade body during use, said front lens being at least a 30 degree lens adapted to expose for indirect observation regions generally above and in front of said front lens; and a retention device affixed to said body and being adapted for slidably receiving said endoscope therein, allowing said endoscope to be slidingly extended and withdrawn relative to said distal end; and said body being shaped for shielding the front lens from tissues surrounding the endoscope during use.

2. A telescopic laryngoscope blade as defined in claim 1 in which said body includes a protrusion extending outwardly from an upper surface of said blade when in use, said protrusion being generally above said front lens.

3. A telescopic laryngoscope blade as defined in claim 1 in which said body includes a ridge extending downwardly from an upper surface of said blade, and said ridge extends spaced from but along side said front lens of said endoscope, for protecting the endoscope from tissues along side said blade.

4. A telescopic laryngoscope blade as defined in claim 2 in which said body includes a ridge extending downwardly from an outer edge of said protrusion, said ridge being spaced from but along side said front lens of said endoscope, for protecting the endoscope from tissues alongside said blade.

5. A telescopic laryngoscope blade as defined in claim 1 in which said retention device is an elastic body encircling said endoscope and secured to said body.

6. A telescopic laryngoscope blade as defined in claim 5 in which a portion of the front lens end of said endoscope is sufficiently flexible to yield when pushed into oral tissues.

7. A telescopic laryngoscope blade as defined in claim 1 in which a portion of the front lens end of said endoscope is sufficiently flexible to yield when pushed into oral tissues.

8. A telescopic laryngoscope blade as defined in claim 1 in which said endoscope is a hollow telescope.

* * * * *